US008721179B2

(12) United States Patent
Watanabe et al.

(10) Patent No.: US 8,721,179 B2
(45) Date of Patent: May 13, 2014

(54) MEDICAL BED APPARATUS

(75) Inventors: Koichiro Watanabe, Nasushirobara (JP); Satoru Ohishi, Otawara (JP); Masaki Kobayashi, Otawara (JP); Katsuie Ikawa, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 183 days.

(21) Appl. No.: 13/181,050

(22) Filed: Jul. 12, 2011

(65) Prior Publication Data
US 2012/0014513 A1    Jan. 19, 2012

(30) Foreign Application Priority Data

Jul. 13, 2010 (JP) .................................. 2010-158908

(51) Int. Cl.
A61B 6/04 (2006.01)
A61G 13/04 (2006.01)
A61G 13/02 (2006.01)

(52) U.S. Cl.
USPC .................................... 378/209; 5/600; 5/608

(58) Field of Classification Search
None
See application file for complete search history.

(56) References Cited

U.S. PATENT DOCUMENTS

| 5,179,746 | A | 1/1993 | Rogers |
| 5,388,294 | A | 2/1995 | Reeder |
| 5,678,267 | A | 10/1997 | Kinder |
| 6,422,241 | B1 * | 7/2002 | Soukal .......................... 128/845 |
| 7,341,375 | B2 | 3/2008 | Zaiki |
| 2003/0021386 | A1 * | 1/2003 | Tanaka ........................... 378/198 |
| 2004/0125920 | A1 * | 7/2004 | Zaiki ............................... 378/195 |
| 2007/0200396 | A1 * | 8/2007 | Baumann et al. .............. 297/135 |
| 2009/0299689 | A1 * | 12/2009 | Stubben ......................... 702/154 |

FOREIGN PATENT DOCUMENTS

| CN | 102327127 A | 1/2012 |
| DE | 33 42 978 A1 | 6/1985 |
| EP | 1 188 637 A2 | 3/2002 |
| EP | 1 530 959 A1 | 5/2005 |
| FR | 604.464 | 5/1926 |
| FR | 2 901 122 A1 | 11/2007 |
| JP | 9-140693 A | 6/1997 |
| JP | 2000-201915 A | 7/2000 |
| JP | 2003-24327 A | 1/2003 |
| JP | 2008-11960 A | 1/2008 |
| JP | 2009-537197 A | 10/2009 |
| WO | WO 2007/135252 A1 | 11/2007 |

OTHER PUBLICATIONS

Combined Chinese Office Action and Search Report Issued Aug. 3, 2012 in Patent Application No. 201110195133.5 (with English translation and English translation of Categories of Cited Documents).
Office Action issued Apr. 2, 2013, in Chinese Patent Application No. 201110195133.5 (with English-language translation).

* cited by examiner

Primary Examiner — Hoon Song
Assistant Examiner — Danielle Fox
(74) Attorney, Agent, or Firm — Oblon, Spivak, McClelland, Maier & Neustadt, L.L.P.

(57) ABSTRACT

A medical bed apparatus of an embodiment includes: a tiltable top board on which to place an examinee; a photographic mechanism configured to radiograph the examinee; an operation unit which is provided to a lateral side of the top board, and through which at least one of the top board and the photographic mechanism is operated by an operator; and a horizontally-holding mechanism configured to hold the operation unit horizontally when the top board tilts.

8 Claims, 5 Drawing Sheets

MEDICAL BED APPARATUS

CROSS-REFERENCE TO THE RELATED APPLICATION

This application is based on and claims the benefit of priority from Japanese Patent Application No. 2010-158908, filed on Jul. 13, 2010; the entire contents of which are incorporated herein by reference.

FIELD

Embodiments relate to a medical bed apparatus on which to place an examinee who is given an image diagnosis or undergoes medical treatment, for example, by use of a radiographing system, an X-ray CT (computed tomography) system, a magnetic resonance imaging system, a nuclear medicine system, and the like.

BACKGROUND

The image diagnosis technology in the field of the radiographing system, the X-ray CT system, the magnetic resonance imaging system, the nuclear medicine system and the like has rapidly evolved in conjunction with the development of the computer technology in these years, and has become essential for the medical treatment today.

For example, the radiographing system becomes in use not only in the medical examination field but also in the medical treatment field, and surgical techniques termed as IVR (interventional radiology) are performed. IVR is a medical treatment given to an affected area by advancing a catheter in blood vessels, organs and the like of an examinee with reference to X-ray fluoroscopic images obtained by radiating X-rays onto the examinee at various angles. Here, various instruments are attached to an extremity of the catheter.

A radiographing system for performing such IVR usually includes: a bed apparatus including a top board on which to place an examinee; an X-ray tube configured to radiate X-rays onto the examinee; an X-ray detector configured to detect the X-rays transmitted through the examinee; a supporting apparatus configured to support the X-ray tube and the X-ray detector in positions opposed to each other; an operation unit through which to operate the bed apparatus and the supporting apparatus; and a control unit configured to control the operations of the bed apparatus and the supporting apparatus on the basis of the manipulation of the operation unit.

In addition, the bed apparatus is capable of a vertical movement to move the top board, where to place the examinee, in the vertical direction, a level movement to slide the top board in the longitudinal and/or lateral direction (a direction orthogonal to the longitudinal direction) thereof, and a standing-and-falling (tilt) movement to tilt the top board in the longitudinal and lateral directions. Furthermore, the supporting apparatus is capable of performing rotary operations in which, for example, the X-ray tube and the X-ray detector opposed to each other are rotated with respect to the longitudinal direction of the top board; and another rotary operation in which the X-ray tube and the X-ray detector are rotated with respect to the lateral direction of the top board. Moreover, the operation unit is provided to a lateral side of the top board and enables an operator, such as a physician or a radiographer, who operates the radiographing system to operate the bed apparatus and the supporting apparatus beside the examinee lying on the top board when necessary.

Incidentally, examples of the supporting apparatus include: a type which runs on the ceiling; and a type which is installed on the floor. These types of supporting apparatuses perform the same rotary operations.

The operation unit is provided to the lateral side of the top board. Once the top board is tilted in the longitudinal direction or in the lateral direction, the operation unit is tilted together in the same direction. This case entails a problem that the operator has difficulty manipulating the operation unit.

Additionally, as is often the case, a rear end portion of the top board on which the examinee does not lie (that is to say, a vacant space near the feet of the examinee) is used as a space for placing things such as a tray and a container to hold surgical instruments and tools. However, once the top board is tilted in the longitudinal direction or in the lateral direction, the tray, the container and the like may fall from the top board.

DETAILED DESCRIPTION

In an embodiment, a medical bed apparatus includes: a tiltable top board on which to place an examinee's body; a photographic mechanism configured to radiograph the examinee's body; an operation unit which is provided to a lateral side of the top board, and through which at least one of the top board and the radiographing mechanism is operated by an operator; and a horizontally-holding mechanism configured to hold the operation unit horizontally when the top board tilts.

Various Embodiments will be described hereinafter with reference to the accompanying drawings.

Referring to FIGS. 1 to 7, detailed descriptions will be hereinbelow provided for a medical bed apparatus of an embodiment of the present invention. Before starting the description, let us explain an overall configuration of a radiographing system including the medical bed apparatus of the embodiment of the present invention. It should be noted that same or similar reference signs denote same or similar parts throughout FIGS. 1 to 7.

Figure 1:
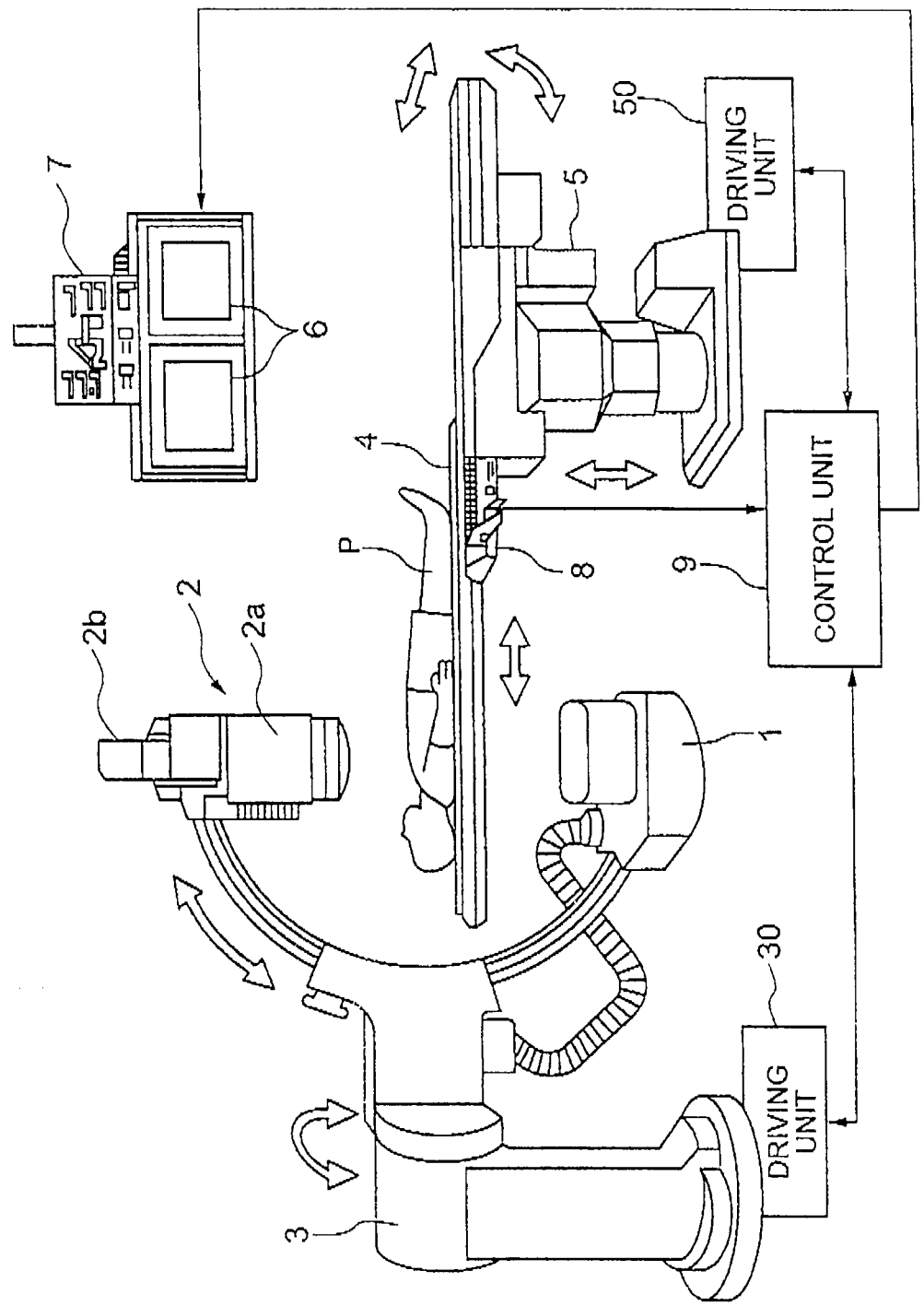
FIG. 1 is a diagram schematically showing an overall configuration of a radiographing system which includes a medical bed apparatus of an embodiment of the present invention.

FIG. 1 schematically shows an overall configuration of the radiographing system. This radiographing system includes; an X-ray tube 1 configured to radiate X-rays onto an examinee P as the examinee's body; an X-ray detector 2 configured to detect the X-rays having been radiated from the X-ray tube 1 and passed through the examinee P; and a supporting apparatus 3 including a driving unit 30 configured to hold the X-ray tube 1 and the X-ray detector 2, and to move the X-ray tube 1 and the X-ray detector 2 in a LAO (Left Anterior Oblique)/RAO (Right Anterior Oblique) direction and in a CAU (Caudal)/CRA (Cranial) direction. The radiographing system further includes: a medical bed apparatus (hereinafter referred to as a "bed apparatus" simply) 5 including a top board 4 on which to place the examinee P; and a driving unit 50 configured to move the medical bed 5 vertically, and to cause the top board 4 to reciprocate in horizontal directions (i.e., in a longitudinal and/or lateral direction), as well as to tilt the top board 4 in the longitudinal and/or lateral direction. These movement directions are marked with double arrows.

The radiographing system further includes: a monitor 6 configured to display a radiograph; a display panel 7 configured to display the current positions of the X-ray tube 1, the X-ray detector 2 and the top board 4, respectively; an operation unit 8 provided to the lateral side of the top board 4 and including push buttons and levers or the like through which to operate the supporting apparatus 3, the bed apparatus 5 and the like, as well as provided to a lateral side of the top board 4; and a control unit 9 configured to control the drive of the driving unit 30, the drive of the driving unit 50, photographic conditions, and the like.

As the X-ray detector 2, an X-ray detector including an image intensifier 2a and a TV camera 2b is shown in FIG. 1. It should by noted, however, that the X-ray detector 2 may be instead a flat panel detector (FPD: flat panel X-ray detector) including semiconductor X-ray detecting elements which are arrayed in a matrix.

Figure 2:
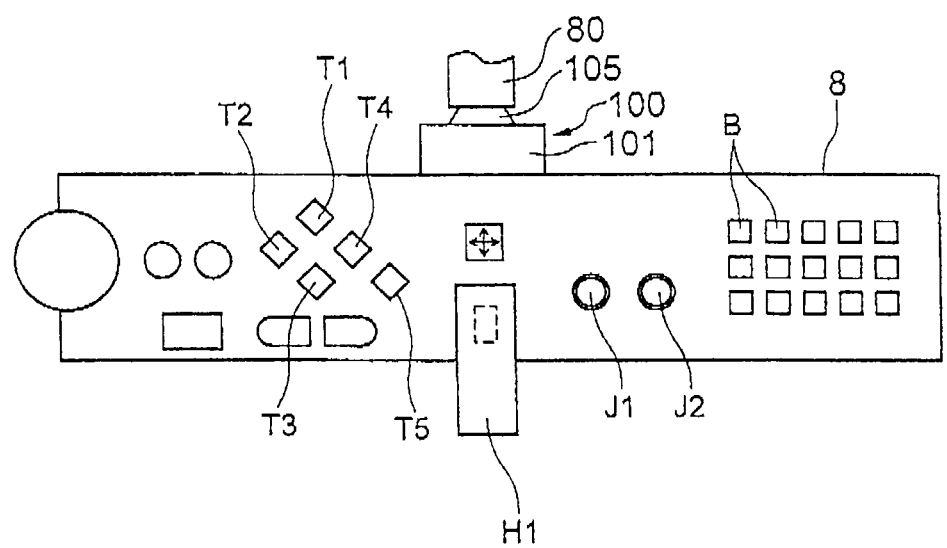
FIG. 2 is a plan view showing an operation unit included in the medical bed apparatus of the embodiment of the present invention.

As shown in FIG. 2, the operation unit 8 includes multiple tilt buttons T1 to T5, a handle H1, multiple joysticks J1, J2, and multiple buttons B. The tilt buttons T1 to T5 are buttons used to adjust the tilt direction and angle of the top board 4. The handle H1 is a handle used to operate the supporting apparatus 3. For example, when an operator such as a physician or a radiographer manipulates this handle H1, the supporting apparatus 3 is accordingly operated in order that the X-ray tube 1 and the X-ray detector 2 should move to their respective desired photographing positions. Either of the joysticks J1, J2 is a joystick used to operate an X-ray stop device (not illustrated) provided in the supporting apparatus 3. Incidentally, the X-ray stop device is a device to adjust an X-ray irradiation field. The buttons B are those used to select a desired photographic condition from multiple photographic conditions, or to select a desired image processing operation from multiple image processing operations. As described above, the operation unit 8 is that used for the operator to operate the photographic mechanism and the top board 4 for the purpose of photographing the examinee P.

It should be noted that the operation unit 8 is not limited to the above-described all-in-one operation unit. For example, a separate-type operation unit may be instead used as the operation unit 8. In this case, the operation unit 8 can be built up by combining necessary functions freely.

When radiographing is performed by use of the thus-configured radiographing system, the operator, such as the physician or the radiographer, positions an area of a photographic target in the examinee P to almost the center of a line joining the X-ray tube 1 and the X-ray detector 2. Here, the area of the photographic target is positioned by adjusting the height of the bed apparatus 5, as well as moving the top board 4 in the direction of the examinee's body axis and in the direction of the examinee's body width, in response to the operator's manipulation of the operation unit 8 with the examinee P laid on the top board 4. In addition, the operator performs a position adjustment by tilting the top board 4 in the longitudinal and/or lateral direction depending on the necessity. These operations are achieved by the control unit 9's controlling the operation of the driving unit 50 on the basis of operation signals from the operation unit 8.

Subsequently, the operator adjusts the X-ray tube 1 and the X-ray detector 2 by driving the supporting apparatus 3 in response to the operator's manipulation of the operation unit 8 in order that the X-ray tube 1 and the X-ray detector 2 can be directed in the respective desired photographic directions, that is to say, in the LAO/RAO direction and in the CAU/CRA direction. This operation is achieved by the control unit 9's controlling the operation of the driving unit 30 on the basis of operation signals from the operation unit 8 as well.

Once determining the position of the examinee P and the photographic direction, the operator steps on a foot switch (not illustrated) provided near the bed apparatus 5. Thereby, X-rays are radiated from the X-ray tube 1, and radiographic images are detected by the X-ray detector 2. Thus, the radiographic images are displayed on the monitor 6. Hence, the physician does things such as insert a catheter and carry out surgical operation while observing the radiographic images displayed on the monitor 6.

Meanwhile, the tilting of the top board 4 in the longitudinal and/or lateral direction makes it difficult for the operator to manipulate the operation unit 8, because the operation unit 8 tilts in the same direction in conjunction with the tilt of the top board 4. With this taken into consideration, the operation unit 8 is connected to the top board 4 in the medical bed apparatus of the embodiment of the present invention in order that the operation unit 8 can be held horizontally even when the top board 4 tilts. Descriptions will be hereinbelow provided for this connecting means.

Example 1

Figure 3:
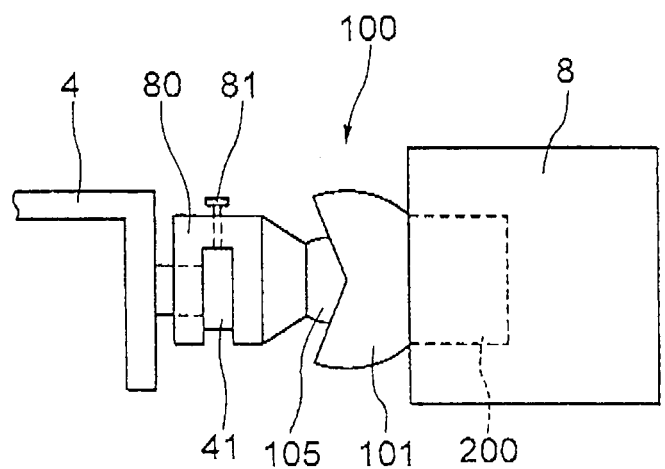
FIG. 3 is a diagram for conceptually explaining a main part of Example 1 of the medical bed apparatus of the embodiment of the present invention.

FIG. 3 schematically shows an embodiment of the medical bed apparatus including such connecting means. This embodiment is that in which the top board 4 and the operation unit 8 are connected together with a spherical piezoelectric motor 100 interposed in between. To put it specifically, a rail 41 serving as a guide when the top board 4 is slid in the longitudinal direction is provided to a lateral side of the top board 4. In this respect, the spherical piezoelectric motor 100 provided to the operation unit 8 is engaged with the rail 41 by use of an attachment member 80, and is fixed to the rail 41 by use of a stopper 81.

Figure 4:
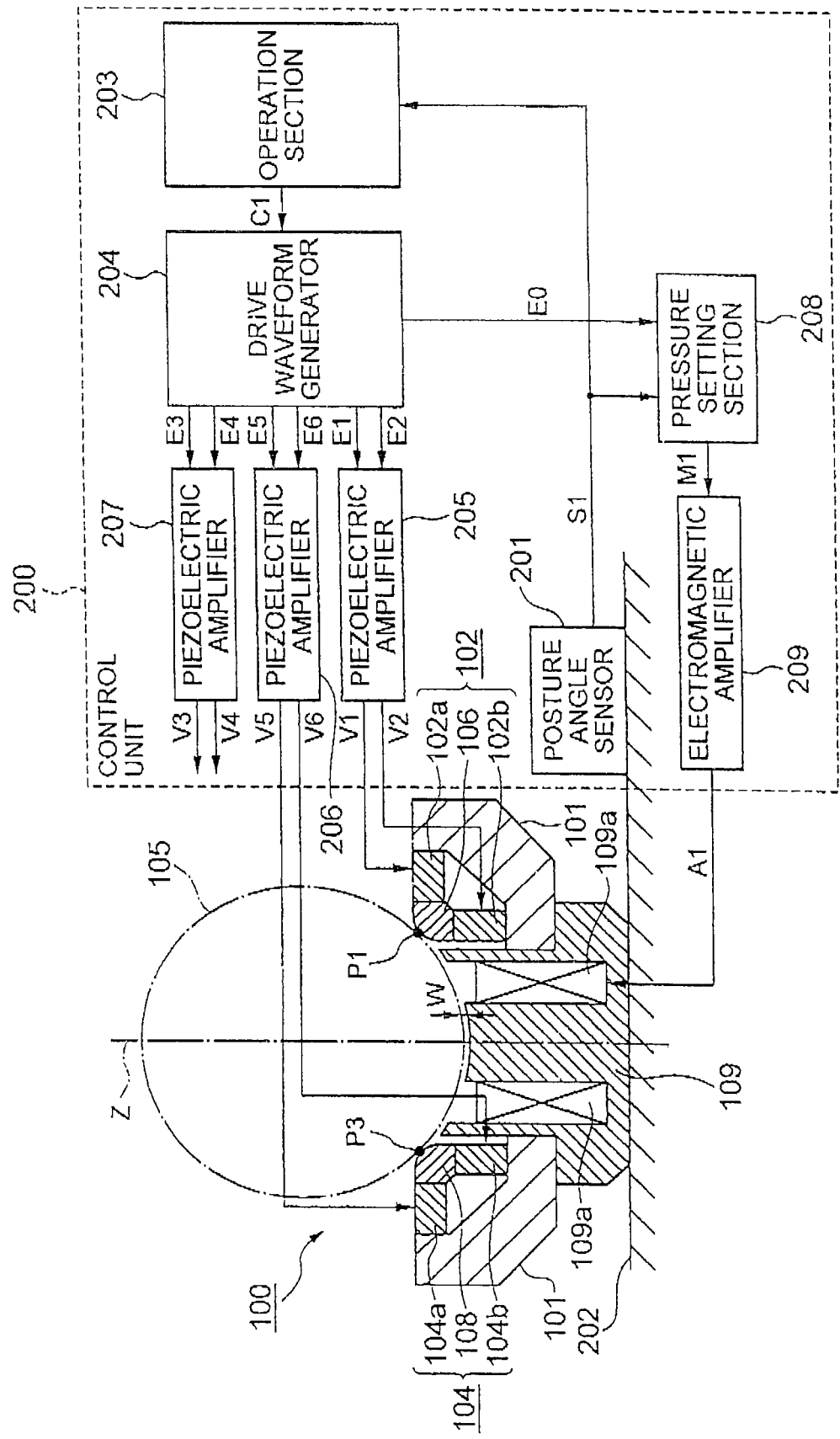
FIG. 4 is a block diagram showing an example of a structural body of a spherical piezoelectric motor and its control system of Example 1.
Figure 5:
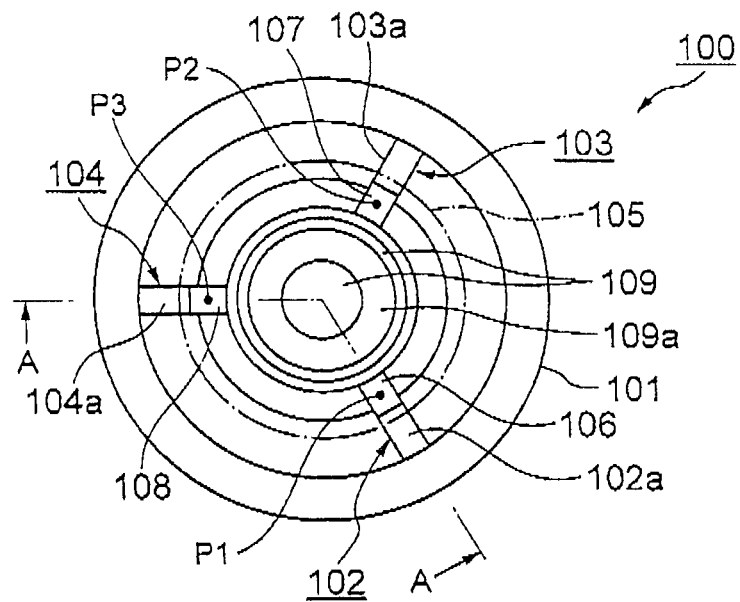
FIG. 5 is a top plan view of the spherical piezoelectric motor shown in FIG. 4.

This spherical piezoelectric motor 100 includes a spherical body 105, a base 101, and a piezoelectric motor system controller 200. The configuration is shown in FIGS. 4 and 5. Although later described in detail with reference to FIGS. 4 and 5, the spherical body 105 is magnetically attracted in a noncontact manner to an electromagnet 109 included in the base 101. The attachment member 80 is fixed to the spherical body 105. In addition, the electromagnet 109 included in the base 101 is fixed to the operation unit 8, and the piezoelectric motor system controller 200 controls the operation of the spherical piezoelectric motor 100.

FIG. 4 is a block diagram showing a structural body of the spherical piezoelectric motor 100 and the piezoelectric motor system controller 200 configured to control the spherical piezoelectric motor 100. FIG. 5 is a top view of the spherical body 105 and the electromagnet 109 included in the structural body shown in FIG. 4. Incidentally, the structural body of the spherical piezoelectric motor 100 shown in FIG. 4 is presented as a cross-sectional view of the structural body taken along the A-A line of FIG. 5.

The spherical piezoelectric motor 100 includes: the base 101 shaped almost like a ring; three piezoelectric units 102, 103, 104 provided in the base 101, and configured to support the spherical body 105 rotatably; and the electromagnet 109 provided in the base 101, and configured to give a pressure force to the piezoelectric units 102, 103, 104 by magnetically attracting the spherical body 105 in the noncontact manner. The electromagnet 109 is shaped, for example, like a ring, and is disposed to hold the spherical body 105 on the Z axis with a predetermined clearance W in between. As shown in FIG. 5, the piezoelectric units 102, 103, 104 are provided at intervals of 120 degrees in the circumferential direction about the Z axis shown in FIG. 4, and thus hold the spherical body 105 stably.

In this respect, the first piezoelectric unit 102 includes: a first piezoelectric element 102a disposed to vibrate in a direction almost horizontal to the base 101 and oblique to the driving direction of the spherical body 105; a second piezoelectric element 102b disposed to extend almost perpendicular to the base 101 and to vibrate in a direction almost orthogonal to the vibration direction of the first piezoelectric element 102a; and a driver 106 connecting the first and second piezoelectric elements 102a, 102b together, contacting the spherical body 105 at a contact point P1, and configured to transmit their composite vibrations as a driving force to the spherical body 105 through friction.

In addition, the second piezoelectric unit 103 (refer to FIG. 5) includes: a first piezoelectric element 103a disposed to vibrate in a direction almost horizontal to the base 101, and oblique to the driving direction of the spherical body 105; a second piezoelectric element 103b disposed to extend almost perpendicular to the base 101 and to vibrate in a direction almost orthogonal to the vibration direction of the first piezoelectric element 103a; and a driver 107 connecting the first and second piezoelectric elements 103a, 103b together, contacting the spherical body 105 at a contact point P2, and configured to transmit their composite vibrations as a driving force to the spherical body 105 through friction.

Furthermore, the third piezoelectric unit 104 includes: a first piezoelectric element 104a disposed to vibrate in a direction almost horizontal to the base 101, and oblique to the driving direction of the spherical body 105; a second piezoelectric element 104b disposed to extend almost perpendicular to the base 101 and to vibrate in a direction almost orthogonal to the vibration direction of the first piezoelectric element 104a; and a driver 108 connecting the first and second piezoelectric elements 104a, 104b together, contacting the spherical body 105 at a contact point P3, and configured to transmit their composite vibrations as a driving force to the spherical body 105 through friction.

It should be noted that: the spherical body 105 is supported by the contact points P1, P2, P3 between the spherical body 105 and the respective first, second and third piezoelectric units 102, 103, 104; and accordingly, the position of the spherical body 105 is uniformly determined. With regard to its posture, the spherical body 105 is geometrically rotatably supported by the contact points P1, P2, P3, but the rotational motion of the spherical body 105 is restricted by frictional forces at the contact points P1, P2, P3 between the spherical body 105 and the respective first, second and third piezoelectric units 102, 103, 104. For this reason, the posture of the spherical body 105 is held unchanged unless an external force greater than the frictional forces between the spherical body 105 and the respective first, second and third piezoelectric units 102, 103, 104 works on the spherical body 105.

The piezoelectric motor system controller 200 is a control system to control the relative postures of the first to third piezoelectric units 102, 103, 104 and the spherical body 105 by adjusting the pressure forces of the respective first to third piezoelectric units 102, 103, 104 toward the spherical body 105. To this end, the piezoelectric motor system controller 200 includes: a posture angle sensor 201 provided on a reference surface 202 of the piezoelectric motor system controller 200, which serves as an attachment surface of the spherical piezoelectric motor 100 attached to the operation unit 8; an operation section 203 configured to setup conditions for driving the spherical piezoelectric motor 100; a drive waveform generator 204 connected to the operation section 203; piezoelectric amplifiers 205, 206, 207 connected to the drive waveform generator 204; a pressure setting section 208 connected to the posture angle sensor 201 and the drive waveform generator 204; and an electromagnetic amplifier 209 connected to the pressure setting section 208.

In this respect, the posture angle sensor 201 measures the posture of the spherical piezoelectric motor 100, and transmits posture information S1 to the operation section 203 and the pressure setting section 208. In addition, the operation section 203 transmits an operation signal C1 to the drive waveform generator 204 on the basis of things such as the conditions set up for driving the spherical piezoelectric motor 100. On the basis of the operation signal C1 from the operation section 203, the drive waveform generator 204 generates voltage waveforms (drive signals) E1, E2, E3, E4, E5, E6 to be respectively applied to the first and second piezoelectric elements 102a, 102b, 103a, 103b, 104a, 104b.

To put it specifically, the drive waveform generator 204 supplies the drive signals E1, E2 to the piezoelectric amplifier 205, the drive signals E3, E4 to the piezoelectric amplifier 207, and the drive signals E5, E6 to the piezoelectric amplifier 206. On the basis of these drive signals, the piezoelectric amplifier 205 produces predetermined drive voltages V1, V2, and apply the drive voltages V1, V2 to the first and second piezoelectric elements 102a, 102b of the piezoelectric unit 102, respectively. Similarly, drive voltages V5, V6 produced by the piezoelectric amplifier 206 are applied to the first and second piezoelectric elements 104a, 104b of the piezoelectric unit 104, respectively. Drive voltages V3, V4 produced by the piezoelectric amplifier 207 are applied to the first and second piezoelectric element 103a, 103b of the piezoelectric unit 103, respectively.

Once receiving a maximum value E0 representing the largest one among the drive signals E1 to E6 from the drive waveform generator 204, and the posture information S1 from the posture angle sensor 201, the pressure setting section 208 sets up a pressure value M1 by use of a predetermined table or a calculation expression on the basis of these pieces of information. On the basis of the pressure value M1 from the pressure setting section 208, the electromagnetic amplifier 209 supplies an electric current A1 to a coil 109a of the electromagnet 109 in order to produce a magnetic attraction in accordance with the pressure value M1.

As described above, the spherical body 105 is rotatably supported by the first to third piezoelectric units 102, 103, 104, and is rotationally driven in any directions of two degrees of freedom by a combination of the composite vibrations of the first to third piezoelectric units 102, 103, 104. In sum, the spherical piezoelectric motor 100 is operated by supplying the drive voltages V1, V2, V3, V4, V5, V6 from the piezoelectric amplifiers 205 to 207 to the first and second piezoelectric elements 102a, 102b, 103a, 103b, 104a, 104b of the first to third piezoelectric units 102, 103, 104. Thereby, the posture of the spherical body 105 can be changed to any desired one.

In short, because the top board 4 and the operation unit 8 are connected together with the spherical piezoelectric motor 100 interposed in between, the operating unit 8 can be always held horizontally when the top board 4 is tilted in the longitudinal and/or lateral direction.

In other words, the posture information S1 from the posture angle sensor 201 is initialized in order that, while the top board 4 is put horizontally, the operation unit 8 should be put horizontally as well. Accordingly, once receiving the posture information S1 from the posture angle sensor 201 while the top board 4 is put horizontally, the piezoelectric motor system controller 200 operates the spherical piezoelectric motor 500 in order to hold the operation unit 8 horizontally.

In addition, once the top board 4 tilts in the longitudinal and/or lateral direction, the tilt direction and angle are detected by the posture angle sensor 201. The information S1 on the detected tilt direction and angle is supplied to the operation section 203 and the pressure setting section 208. The first to third piezoelectric units 102, 103, 104 try to rotate the spherical body 105 in accordance with the detected tilt direction and angle. Because, however, the spherical body 105 is fixed to the top board 4 by use of the attachment member 80, the first to third piezoelectric units 102, 103, 104 supporting the spherical body 105 move in a direction opposite to the tilt direction of the top board 4. Accordingly, the base 101 rotationally moves in the direction opposite to the tilt direction of the top board 4 by the tilt angle, where the tilt direction and angle are detected by the posture angle sensor 201. Thereby, the operation unit 8, to which the base 101 is fixed, can be held horizontally irrespective of the tilt of the top board 4.

As described above, the embodiment of the present invention makes it possible to hold the operation unit 8 horizontally irrespective of the tilt direction and angle of the top board 4. This makes it possible to easily operate the radiographing system and the bed apparatus when IVR or the like is performed.

It should be noted that the horizontally-holding mechanism horizontally holding the operation unit 8 when the top board 4 tilts as described above functions as an adjustment mechanism capable of adjusting the tilt of the operation unit 8 relative to the board 4. In addition, the spherical piezoelectric motor 100 functions as a driver to drive the operation unit 8 to offset the tilt of the operation unit 8 in accordance with the tilt direction and angle of the top board 4 detected by an angle sensor, for example, the posture angle sensor 201.

Furthermore, the horizontally-holding mechanism may be built to allow the tilt of the operation unit 8 relative to the top board 4 to be adjusted manually, that is, to allow the operator to tilt the operation unit 8 relative to the top board 4. In this case, the horizontally-holding mechanism is built in a way that, when the operator manipulates the operation unit 8, the tilt operation of the operation unit 8 relative to the top board 4 can be switched between its fixation and release. The operator releases the tilt operation of the operation unit 8 relative to the top board 4, for example, by pressing a button in the operation unit 8, and turns the operation unit 8 from the tilted state to the horizontal state. Subsequently, the operator fixes and prohibits the tilt operation of the operation unit 8 relative to the top board 4 by pushing a button in the operation unit 8 again. By this, the operation unit 8 can be held horizontally irrespective of the tilt direction and angle of the top board 4.

Example 2

As Example 2, another embodiment of the medical bed apparatus will be described with reference to FIG. 6.

Figure 6:
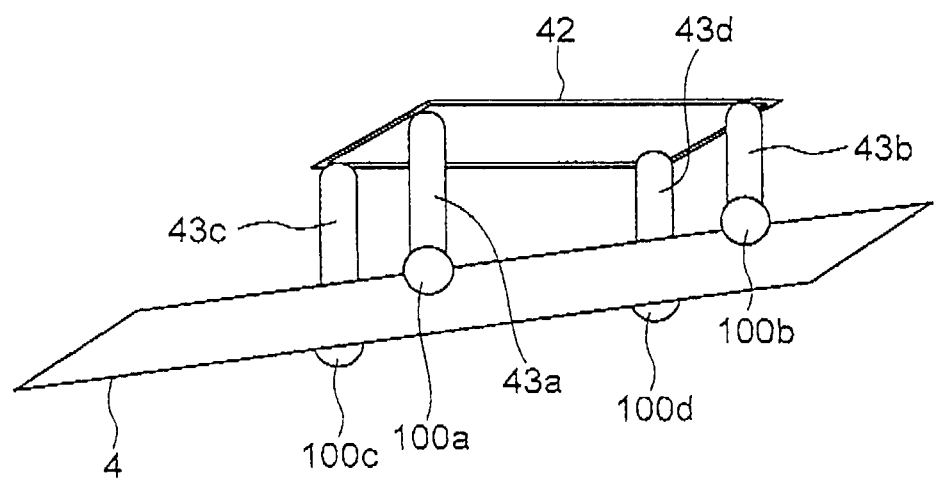
FIG. 6 is a diagram for conceptually explaining a main part of Example 2 of the medical bed apparatus of the embodiment of the present invention.

FIG. 6 is a diagram shown for the purpose of explaining the concept of Example 2. Example 2 aims at providing means for solving a problem that: when the top board 4 is tilted in the longitudinal and/or lateral direction during the performing of IVR, a rear end portion of the top board 4 on which the examinee P does not lie (in other words, a vacant space near the feet of the examinee P), and which is used as a space for placing things such as a tray and a container to hold surgical instruments and tools therein, tilts in conjunction with the tilt of the top board 4; and the tray, the container and the like accordingly fall from the top board 4.

A tray 42 is placed on an upper surface of the rear portion of the top board 4. The tray 42 functions as a table on which to place articles. Four corners of this tray 42 are supported, respectively, by four legs 43a, 43b, 43c, 43d which are formed expandable and contractible. The legs 43a, 43b, 43c, 43d are supported by spherical piezoelectric motors 100 of the same type shown in FIGS. 4 and 5. It should be noted that in FIG. 6, the spherical piezoelectric motors are denoted by reference signs 100a, 100b, 100c, 100d respectively associated with the legs 43a, 43b, 43c, 43d for the sake of explanatory convenience. In addition, the spherical piezoelectric motors 100a, 100b, 100c, 100d include their respective piezoelectric motor system controllers 200, and are attached to rails 41 provided to the two lateral sides of the top board 4, which serve as guides when the top board 4 is slid in the longitudinal direction.

Although not illustrated, small-sized motors are built in the insides of the legs 43a, 43b, 43c, 43d, respectively. These small-sized motors are power sources configured to expand and contract the legs 43a, 43b, 43c, 43d, respectively. Incidentally, while the top board 4 is in the horizontal position, the heights of the respective legs 43a, 43b, 43c, 43d are shortest, and the tray 42 supported by these legs 43a, 43b, 43c, 43d is accordingly held horizontally.

In this respect, when the top board 4 tilts, for example, in the longitudinal direction, the tilt angle of the top board 4 is detected by posture angle sensors 201 of the piezoelectric motor system controllers 200 included in the legs 43a, 43b, 43c, 43d, respectively. The tilt angle detected by the posture angle sensors 201 is converted to drive signals for the spherical piezoelectric motors 100a, 100b, 100c, 100d which hold the legs 43a, 43b, 43c, 43d, respectively. Thus, the piezoelectric motor system controllers 200 operate in order to rotate the spherical piezoelectric motors 100a, 100b, 100c, 100d in a direction opposite to the detected tilt direction by the detected tilt angle. Accordingly, the legs 43a, 43b, 43c, 43d supporting the tray 42 tilt in the opposite direction. The same applies to the case where the top board 4 is tilted in the lateral direction.

In particular, if the operation of the spherical piezoelectric motors 100a, 100b, 100c, 100d would hold the tray 42 horizontally by tilting the legs 43a, 43b, 43c, 43d in the direction opposite to the tilt direction of the top board 4 by the tilt angle, progressive increase in the tilt angle of the top board 4 would lead to interference of the tray 42 with the surface of the top board 4 and shift of the tray 42 in the height direction. With this taken into consideration, the tilt angle detected by the posture angle sensors 201 is supplied as drive signals to the small-sized motors built in the legs 43a, 43b, 43c, 43d, respectively. Because the four legs 43a, 43b, 43c, 43d have their expandable and contractible structures, the heights of the legs 43a, 43b, 43c, 43d are adjusted in order to make the tray 42 keep its horizontal state by driving the small-sized motors in accordance with the detected tilt angle, respectively.

As described above, the tray 42 above the top board 4 can be held in the horizontal state by adjusting the rotations of the spherical piezoelectric motors 100a, 100b, 100c, 100d and the heights of the legs 43a, 43b, 43c, 43d, which operate in accordance with the tilt angle of the top board 4 detected by the posture angle sensors 201. Accordingly, the space on which to place the surgical instruments and tools needed when a manual surgical technique such as IVR is performed can be secured above the top board 4.

It should be noted that even when the spherical piezoelectric motors 100a, 100b, 100c, 100d are replaced with simple spherical bearings, the tray 42 can be held in the horizontal state in a simple manner. In addition, the heights of the legs 43a, 43b, 43c, 43d may be expanded and contracted manually instead of by the small-sized motors.

It should be noted that the horizontally-holding mechanism horizontally holding the tray 42 when the top board 4 tilts as described above functions as the adjustment mechanism capable of adjusting the tilt of the tray 42 relative to the top board 4. In addition, the small-sized motors and the spherical piezoelectric motors 100a, 100b, 100c, 100d function as drivers to expand and contract the legs 43a, 43b, 43c, 43d in order to offset the tilt of the tray 42 in accordance with the tilt direction and angle of the top board 4 detected by the angle sensors, for example, the posture angle sensors 201.

Moreover, the horizontally-holding mechanism may be configured to enable the tilt of the tray 42 to be manually adjusted relative to the top board 4, that is to say, to enable the operator to tilt the tray 42 relative to the top board 4. In this case, the horizontally-holding mechanism is configured to switch the tilt operation of the tray 42 relative to the top board 4 between its fixation and release through the manipulation of the operation unit 8 by the operator. The operator releases the tilt operation of the tray 42 relative to the top board 4, for example, by pressing a button in the operation unit 8, and thereby turns the tray 42 from the tilted state to the horizontal state. Thereafter, the operator fixes and prohibits the tilt operation of the tray 42 relative to the top board 4 by pressing a button in the operation unit 8 again. This makes it possible to hold the tray 42 horizontally irrespective of the tilt direction and angle of the top board 4.

Example 2

As Example 3, yet another embodiment of the medical bed apparatus will be described with reference to FIG. 7.

Figure 7:
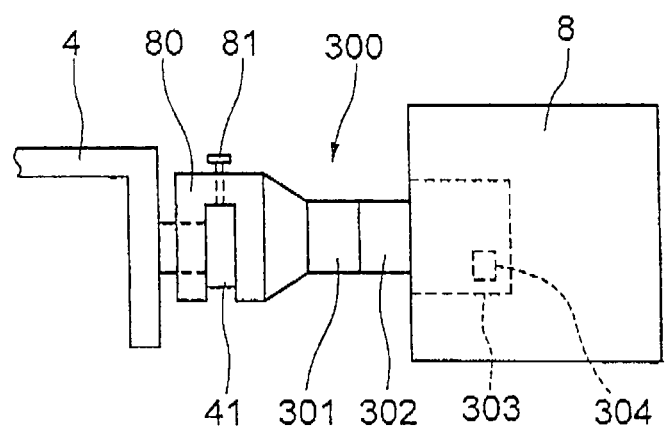
FIG. 7 is a diagram for conceptually explaining a main part of Example 3 of the medical bed apparatus of the embodiment of the present invention.

FIG. 7 is a diagram shown for the purpose of explaining the concept of Example 3. Example 3 aims at providing means for solving a problem that, when the top board 4 is tilted in the longitudinal and/or lateral direction during the performing of IVR, the operator has difficulty manipulating the operation unit 8 because the operation unit 8 tilts together in the same direction. Example 3 is a modification of the connecting means of Example 1.

This embodiment is that in which the top board 4 and the operation unit 8 are connected together with a two-axis motor 300 interposed in between. To put it specifically, a rail 41 serving as a guide when the top board 4 is slid in the longitudinal direction is provided to a lateral side of the top board 4. In this respect, the two-axis motor 300 provided to the operation unit 3 is engaged with the rail 41 by use of an attachment member 80, and is fixed to the rail 41 by use of a stopper 81.

This two-axis motor 300 includes a first-axis motor 301, a second-axis motor 302 and a motor system controller 303. The first-axis motor 301 is configured to drive the operation unit 8 in the same direction as the top board 4 rotates when the top board 4 tilts in the longitudinal direction. The second-axis motor 302 is configured to drive the operation unit 8 in the same direction as the top board 4 rotates when the top board 4 tilts in the lateral direction. The first-axis motor 301 and the second-axis motor 302 enable the operation unit 8 to be driven in a direction opposite to the tilt direction of the top board 4.

The motor system controller 303 is a control system to control the relative postures of the top board 4 and the operation unit 8 by adjusting the number of revolutions of the first-axis motor 301 and the number of revolutions of the second-axis motor 302. To this end, the motor system controller 303 includes a posture angle sensor 304 provided in the reference surface of the motor system controller 303, which is an attachment surface of the two-axis motor 300 attached to the operation unit 8. This posture angle sensor 304 is configured to measure the posture of the operation unit 8.

As described above, the operation unit 8 can be held by the two-axis motor 300, and concurrently can be rotationally driven in predetermined directions of two degrees of freedom by the two-axis motor 300. To put it specifically, the supplying of a drive voltage from the motor system controller 303 to the first-axis motor 301 or the second-axis motor 302 makes it possible to arbitrarily change the posture of the operation unit 8 by operating the first-axis motor 301 or the second-axis motor 302.

In sum, because the top board 4 and the operation unit 8 are connected together with the two-axis motor 300 interposed in between, the operation unit 8 can be always held horizontally when the top board 4 is tilted in the longitudinal and/or lateral direction.

In other words, the posture information from the posture angle sensor 304 is initialized in order that, while the top board 4 is put horizontally, the operation unit 8 should be put horizontally as well. Accordingly, once receiving the posture information from the posture angle sensor 304 while the top board 4 is put horizontally, the motor system controller 303 operates the two-axis motor 300 in order to hold the operation unit 8 horizontally.

In addition, once the top board 4 tilts in the longitudinal and/or lateral direction, the tilt direction and angle are detected by the posture angle sensor 304. The information on the detected tilt direction and angle is supplied to the motor system controller 303. In accordance with the detected tilt direction and angle, the motor system controller 303 rotates the first-axis motor 301 and the second-axis motor 302 in a direction opposite to the tilt direction of the top board 4. Accordingly, the operation unit 8 rotationally moves in the direction opposite to the tilt direction of the top board 4 by the tilt angle, where the tilt direction and angle are detected by the posture angle sensor 304. This makes it possible to hold the operation unit 8 horizontally irrespective of the tilt of the top board 4.

As described above, the embodiment of the present invention enables the operation unit 8 to be held horizontally irrespective of the tilt direction and angle of the top board 4. This makes it possible to easily operate the radiographing system and the bed apparatus while IVR and the like are carried out.

It should be noted that the two-axis motor 300 functions as a driver to drive the operation unit 8 in order to offset the tilt of the operation unit 8 in accordance with the tilt direction and angle of the top board 4 detected by the angle sensor, for example, the posture angle sensor 304. In addition, even in a case where the foregoing two-axis motor 300 is used as the spherical piezoelectric motor 100a, 100b, 100c, 100d in Example 2, it is possible to obtain the same effects as can be obtained from Example 2.

At least one of the foregoing embodiments enables the operation unit 8 or the tray, 42 to be horizontally held by the horizontally-holding mechanism irrespective of the tilt direction and angle of the top board 4.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical bed apparatus comprising:
a tiltable top board on which to place an examinee;
a photographic mechanism configured to radiograph the examinee;
an operation unit which is provided to a lateral side of the top board, and through which at least one of the top board and the photographic mechanism is operated by an operator; and
a horizontally-holding mechanism configured to hold the operation unit horizontally when the top board tilts, wherein
the horizontally-holding mechanism comprises:
an angle sensor configured to detect a tilt direction and a tilt angle of the top board; and
a driving unit configured to drive the operation unit to offset the tilt of the operation unit in accordance with the tilt direction and the tilt angle of the top board which are detected by the angle sensor.

2. The medical bed apparatus of claim 1, wherein
the driving unit is a spherical piezoelectric motor interposed between the top board and the operation unit.

3. A medical bed apparatus comprising:
a tiltable top board on which to place an examinee;
a photographic mechanism configured to radiograph the examinee;
an operation unit which is provided to a lateral side of the top board, and through which at least one of the top board and the photographic mechanism is operated by an operator; and
a horizontally-holding mechanism configured to hold the operation unit horizontally when the top board tilts, wherein
the horizontally-holding mechanism is formed to allow the operator to tilt the operation unit relative to the top board, and
the horizontally-holding mechanism is formed to switch a tilt operation of the operation unit relative to the top board between its fixation and release in response to an operator's manipulation of the operation unit.

4. A medical bed apparatus comprising:
a tiltable top board on which to place an examinee;
a plurality of expandable and contractible legs provided to the top board;
a horizontally-holding mechanism configured to hold the table horizontally when the top board tilts, wherein
the horizontally-holding mechanism comprises:
an angle sensor configured to detect a tilt direction and a tilt angle of the top board; and
a driving unit configured to expand, contract and drive the plurality of legs to offset the tilt of the table in accordance with the tilt direction and the tilt angle of the top board detected by the angle sensor.

5. The medical bed apparatus of claim 4, wherein
the driving unit comprises a plurality of spherical piezoelectric motors interposed between the top board and the plurality of legs.

6. The medical bed apparatus of claim 4, wherein
the top board is formed tiltable in at least longitudinal and lateral directions.

7. The medical bed apparatus of claim 4, wherein
the horizontally-holding mechanism is formed to allow the operator to tilt the table relative to the top board.

8. A medical bed apparatus comprising:
a tiltable top board on which to place an examinee;
a plurality of expandable and contractible legs provided to the top board;
a table horizontally supported by the plurality of legs; and
a horizontally-holding mechanism configured to hold the table horizontally when the top board tilts, wherein
the horizontally-holding mechanism is formed to allow the operator to tilt the table relative to the top board, and
the horizontally-holding mechanism is formed to switch a tilt operation of the table relative to the top board between its fixation and release in response to an operator's manipulation of the operation unit.

* * * * *